United States Patent [19]
Cusimano

[11] Patent Number: 5,462,065
[45] Date of Patent: Oct. 31, 1995

[54] INTEGRATED MOVEMENT ANALYZIING SYSTEM

[76] Inventor: MaryRose Cusimano, 1050 Whitney Ranch Dr. #3023, Henderson, Nev. 89014

[21] Appl. No.: 296,013

[22] Filed: Aug. 17, 1994

[51] Int. Cl.$^6$ ........................................ A61B 5/103
[52] U.S. Cl. ........................................ 128/782
[58] Field of Search .................... 128/774, 779, 128/781, 782, 734, 741; 73/379

[56] References Cited

U.S. PATENT DOCUMENTS

| | | | |
|---|---|---|---|
| 4,586,515 | 5/1986 | Berger | 128/782 |
| 4,667,513 | 5/1987 | Konno | 128/774 |
| 4,688,581 | 8/1987 | Moss | 128/741 |
| 4,800,897 | 1/1989 | Nilsson | 128/782 |
| 4,928,709 | 5/1990 | Allison et al. | 128/782 |
| 4,938,476 | 7/1990 | Brunelle et al. | 128/782 |
| 5,012,820 | 5/1991 | Meyer | 128/782 |
| 5,042,505 | 8/1991 | Meyer et al. | 128/781 |

*Primary Examiner*—Max Hindenburg
*Attorney, Agent, or Firm*—Albert O. Cota

[57] ABSTRACT

An integrated movement analyzing system (10) that utilizes surface electromyography in combination with range of motion and functional capacity testing to monitor any muscle group in the human body (80). The system (10) consists of an integrated movement analyzer (18) that receives inputs from up to 32 channels of surface EMG electrodes (12), a range of motion arm (ROMA) (14) having six degrees of freedom, and a functional capacity sensor (FCS) (16) having one output channel. When performing upper and lower back protocol testing, the ROMA (14) is connected between the patient's upper back and lower back by a shoulder harness (40) and a waist belt (42). For cervical testing, the ROMA (14) is connected between the patient's head and upper back by a cervical cap (44) and the shoulder harness (40). The output of the IMA (18) is provided via an analog to digital converter (30) to a computer (34). The computer (34) in combination with a software program (36) produces comparative analytical data which is primarily in the form of graphic plots.

20 Claims, 12 Drawing Sheets

INTEGRATED MOVEMENT ANALYZIING SYSTEM

TECHNICAL FIELD

The invention pertains to the general field of electrodiagnostic equipment and more particularly to an integrated movement analyzing system that combines electromyography with range of motion and functional capacity measurements, to provide a non-invasive and non-loading method for analyzing myofascial injuries.

BACKGROUND ART

Unresolved myofascial injuries represent the second largest medical problem today, with back pain alone accounting for the largest medical visits. Carpal tunnel syndrome (CTS), repetitive stress injuries (RSI) account for the most days lost and are predicted to become the most costly health problem of our time. With the implementation of the American's with disability (ADA) law worker's compensation claims such as CIS can now sue in the federal court system allowing for the initiation of suits in excess of 10 million dollars. These claims could damage the economy and force employers to go outside of the United States.

A recent study in the New England Journal of Medicine indicates that over 58% of asymptomatic low back pain patients who underwent an MRI found evidence of disc pathology. How reliable is an MRI—it appears to have no correlation to pain, impairment and may not be clinically significant.

A recent study revealed that over 45 percent of individuals who have undergone CTS release surgery were no better two years past the surgical intervention because they were misdiagnosed. The individuals probably had cervical pathology that can refer pain and mimic the symptoms of carpal tunnel, ulnar neuopathy, cubital tunnel, tendonititis, DeQuarians syndrome i.e., repetitive stress injuries. The problem is that until the development of the instant invention, there was no way to ascertain if the problem was proximal (cervical or distal CTS).

In the past, many doctors have prescribed a profilastic work restriction limiting the amount an individual can lift. More often than not, the lifting restriction is too general and too limiting which prohibits the individual to return back to their usual and customary job. For example, a typical work restriction of no lifting over 50 pounds is highly restrictive. Doctors impose this restriction because they have no means of evaluating the muscle and disc pathology during movement.

The inventive integrated movement analyzer (IMA) is a portable, non-loading electronic instrument that simultaneously monitors muscle activity with silver chloride standard ECG electrodes, cervical, thoracic and lumbar flexion, extension, right rotation, left rotation, right lateral movement, and left lateral movement. The IMA also simultaneously combines a non loading load cell and strain gauge that with a computer and software correlates the weight lifted by pulling on the strain gage. The EMG, Range of Motion and FCE (functional capacity evaluation) are all conducted at the same time.

The IMA is portable and can be battery operated to allow the patient to be monitored anywhere including at the work sight, at home and performing any activity even their job, no matter what or where it is. The IMA also complies with the new ADA law, and includes a special device that allows for heart rate in the filter system. This is important because when heart rate is found in the paraspinal muscles over the EMG, in the upper trapezius and in the low back, the amplitude of the ECG activity that overlaps the EMG correlates to disc pathology or spinal changes on an MRI. Since the IMA monitors active range of motion, it takes the MRI one step further and can help determine if the monitored ailment, can in fact, be treated with conservative methods that do not involve surgery.

A search of the prior art did not disclose any patents that read directly on the claims of the instant invention. However, the following U.S. patents were considered related:

| U.S. Pat. No. | INVENTOR | ISSUED |
|---|---|---|
| 5,042,505 | Mayer et al | 27 August 1991 |
| 4,688,581 | Moss | 25 August 1987 |
| 4,667,513 | Konno | 26 May 1987 |

The U.S. Pat. No. 5,042,505 Mayer, et al patent discloses an electronic device for measuring relative angular positional displacement and angular range of motion for body segments and articulating joints of the human skeleton. The device has a hand-held interface unit which is placed against the body segment or joint to be tested. Mounted within the housing of the interface unit is a shaft with a pendulum at one end and an optical encoder at the other. As the body segment rotates or the joint articulates, the pendulum swings in the direction of gravity, causing the shaft to rotate. The optical encoder generates an electrical signal representative of the amount of rotation of the shaft. The generated signal is fed to a microprocessor which processes the information and can produce on a display the change in angular position relative to initial angular position or the angular range of motion of the body segment or articulating joint.

The U.S. Pat. No. 4,688,581 Moss patent discloses an apparatus and a method for non-invasive in vivo determination of muscle fiber composition. The method includes the steps of electrically stimulating a chosen muscle; determining the stimulation current; measuring the electrical potential of the muscle; the contraction time; and the force produced by the contraction; and by intercorrelating the data by multiple regression, determining the type, percentage and size of muscle fibers within the muscle stimulated. Apparatus for determining the muscle composition includes a muscle stimulator of controlled voltage; electromyogram equipment; and a force transducer providing a tension curve as well as force measurements.

The U.S. Pat. No. 4,667,513 Konno patent discloses an apparatus and a method for estimating the degree of the fatigue and pain of muscles. The apparatus composes subjects of different weights on the same basis by deriving the variation in the muscular strength such as the dorsal muscular strength, shoulder muscular strength, the grasping power, and the like. An analogous electric signal integrated the muscular output on one hand, and provides an integrated value of the electromyogrammatic amplitude by processing the voltage induced from the muscle to be tested through an electromyogram amplitude and a waveform processor. The ratio between these integrated values, after correcting the ratio with a weight/muscular strength coefficient is digitally displayed.

For background purposes and as indicative of the art to which the invention relates, reference may be made to the following remaining patents found in the search:

| U.S. Pat. No. | INVENTOR | ISSUED |
| --- | --- | --- |
| 5,056,530 | Butler et al | 15 October 1991 |
| 5,050,618 | Larsen | 24 September 1991 |
| 5,038,795 | Roush, et al | 13 August 1991 |
| 5,012,820 | Meyer | 7 May 1991 |
| 4,886,073 | Dillon et al | 12 December 1989 |
| 4,845,987 | Kenneth | 11 July 1989 |
| 4,834,057 | McLeod, Jr. | 30 May 1989 |
| 4,805,636 | Barry et al | 21 February 1989 |
| 4,742,832 | Kauffmann et al | 10 May 1988 |

DISCLOSURE OF THE INVENTION

The integrated movement analyzing system combines electromyography with range of motion and functional capacity measurements to provide doctors and other clinical practitioners with a method for accurately analyzing myofascial injuries. The system in its basic form is comprised of an integrated movement analyzer (IMA) that functions in combination with a surface electromyography (SEMG) cable having a set of non-invasive SEMG electrodes that attach to a patient, a range-of-motion arm (ROMA), and a functional capacity sensor (FCS). The IMA is connected to a computer that produces data representative of the patient's problems being analyzed.

The IMA is a portable, non-loading electronic instrument that incorporates a surface electromyography section that receives and processes the signals produced by the set of SEMG electrodes; a range of motion section that processes the signals from the ROMA; and a functional capacity section that processes the signals from the FCS. The signals from all the sections are routed to an analog-to-digital converter (ADC) that further processes the signals before they are applied to the computer. The IMA has the capability to sample up to 32 channels of the SEMG cable, six channels of the ROMA signals and one channel of the FCS. All the signals are simultaneously measured at sampling speeds of up to 10 KHz for testing time frames.

The ROMA is a non-load bearing electro-mechanical device that includes three articulated sections. When performing back protocol testing, the ROMA is attached from the patient's shoulder to the patient's lower back by use of a shoulder harness. When performing cervical testing, the ROMA is attached from the patient's head to the upper back by use of a cervical cap and the shoulder harness. The FCS produces a signal that is representative of a pulling force exerted by the patient. The FCS is comprised of a strain gauge mounted on a plate on which the patient stands. Attached to the stain gauge is a pull cable having attached to its upper end a handle grip. When the grip is pulled by the patient, the strain gauge measures the patient's pulling force which is analogous to the patient's lifting power. The IMA also includes a lead failure detection section having a circuit that causes a specific LED to illuminate when a corresponding specific lead failure has occurred from a SEMG electrode.

The simultaneous monitoring of the muscle groups allowed by the system measures muscle tone, muscle spasms, muscle activity and response, as well as muscle recovery and fatigue. This is accomplished for each muscle group monitored while several muscles are being monitored at the same time above and below the area of complaint. This allows the analyst with the system, to outline a specific therapy program for the problem and traces the referred pain problem. With the site specific treatment protocol, physical therapy is reduced to 50–60 percent less sessions, decreases costs, treatment time and directs the specific type of treatment like electrical stem, ultra sound massage or nerve block to a specific location. Thus, Medical costs related to treatment and use of medication are greatly reduced.

In view of the above disclosure, it is the primary object of the invention to provide doctors and other diagnostic personnel with a system that simultaneous utilizes surface electromyography in combination with range of motion and functional capacity testing to monitor any muscle groups in the human body.

In addition to the primary object, it is also an object of the invention to provide a system that:

measures compliance without the patient's cooperation. Because the range of motion, FCG are combined with specific EMG readings, the system can tell if the patient could not complete the range of motion or the lifting task. This is very important to the insurance industry to reduce and defer fraudulent worker's compensation and personal injury claims.

includes a specific protocol for carpal tunnel syndrome (CTS) that monitors the testing and range of motion readings for all cervical and upper extremity muscle groups. This interactive protocol with the system allows doctors to look at the relationship between muscle groups and to diagnose if the problem is cervical CTS or cubital tunnel. The system also allows doctors to determine if it is a repetitive stress injury.

is beneficial to sports in that it can tell an athlete what muscle groups to work out with what procedure and for how long before the muscle fatigues; thus, it maximizes the work-out period without casing injury.

is beneficial for pre-employment screening to have a "finger print" of muscle activity if there is a subsequent injury.

can diagnose soft tissue injury.

can tell if disc pathology is present and if it is clinically significant, can provide site-specific treatment protocols, can eliminate the need for most carpal tunnel and cubital tunnel surgeries.

These and other objects and advantages of the present invention will become apparent from the subsequent detailed description of the preferred embodiment and the appended claims taken in conjunction with the accompanying drawings.

THE BEST MODE FOR CARRYING OUT THE INVENTION

Figure 1:
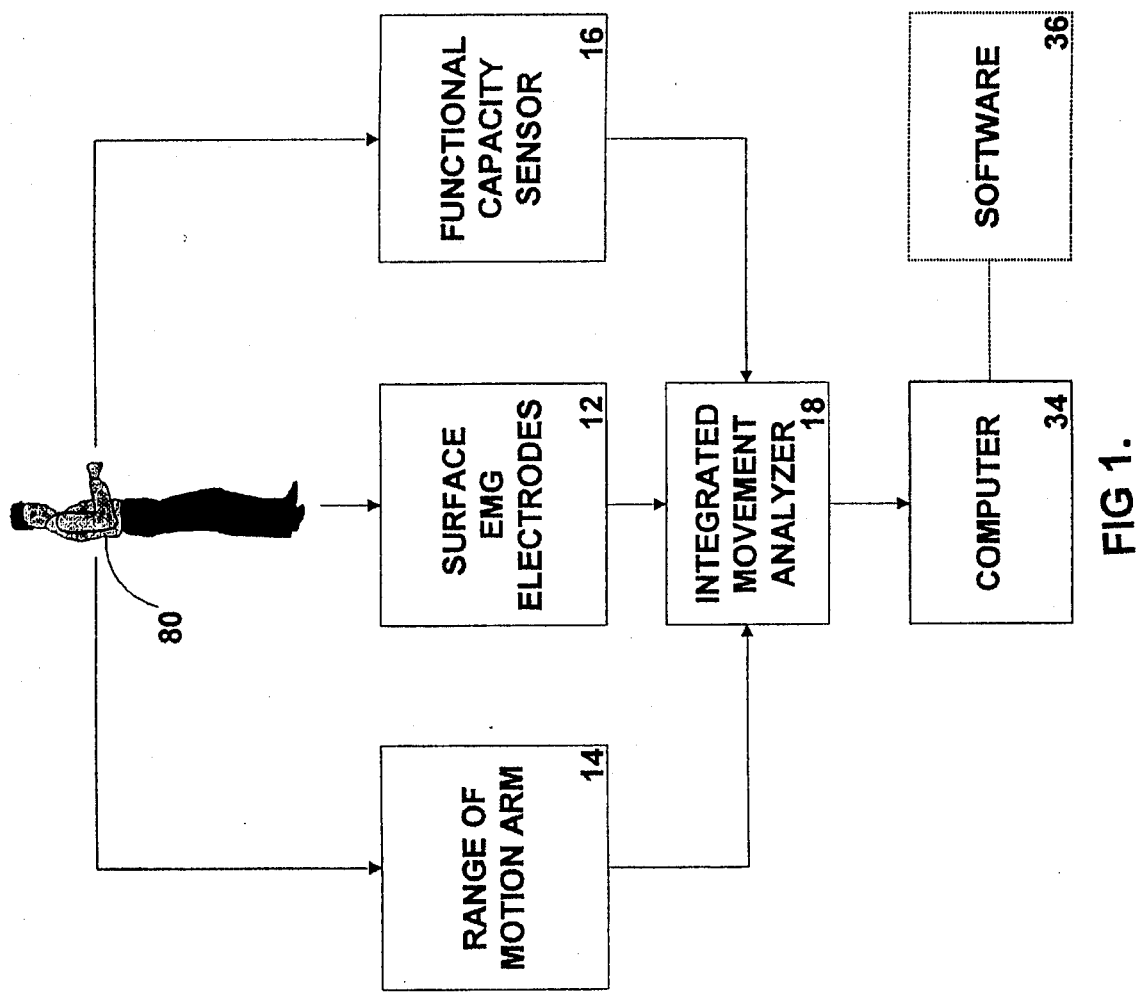
FIG. 1 is a block diagram of the overall of the integrated movement analyzing system.

The best mode for carrying out the invention is presented in terms of a preferred embodiment that utilizes surface electromyography in combination with range of motion and functional capacity testing to monitor any muscle group in the human body.

The preferred embodiment of the integrated movement analyzing system 10 as shown in FIGS. 1–14, is comprised of the following seven major elements: a surface electromyography (SEMG) cable assembly 12, a range of motion arm (ROMA) 14, that operates in combination with a shoulder harness 40, a waist belt 42, and a cervical cap 44; a functional capacity sensor (FCS) 16, an integrated movement analyzer 18, and a computer 34 that operates with software 36.

Figure 2:
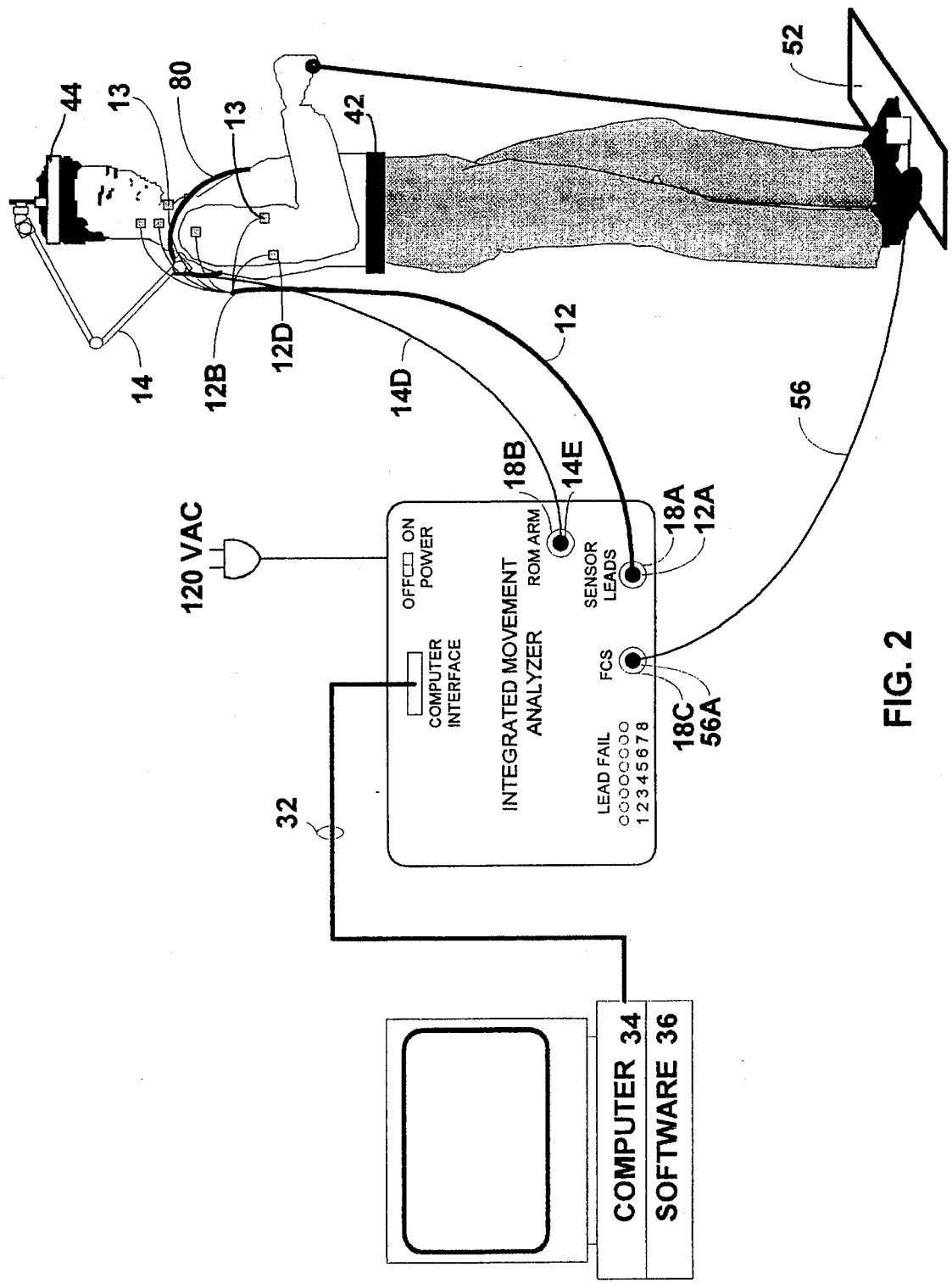
FIG. 2 is a block diagram showing the interface between the integrated movement analyzer, the computer and a patient having the range of motion arm attached to a patient by means of a cervical cap and shoulder harness.

The overall integrated movement analyzing system 10 is shown in FIGS. 1 and 2. As shown in the figures, the integrated movement analyzer (IMA) 18 is the focal point of the system 10 and receives inputs from the surface electromyography (SEMG) electrodes 12, the range of motion arm (ROMA) 14 and the functional capacity sensor (FCS) 16; all of which are connected to a human patient 80. The output of the IMA 18 is provided to the computer 34 which produces comparative analytical data which is primarily in the form of graphic plots.

The surface electromyograph (SEMG) cable assembly 12 as shown in FIG. 2, has on one end a male twist-lock connector 12A, and from the other end extends a set of electrodes 12B. In FIG. 2, only four electrodes are shown for illustrative purposes; in the actual cable design, the electrodes can number from 8 to 32 and preferably consist of standard silver chloride electrodes. The male connector 12A is sized to be attached to a mating female connector 18A located in the integrated movement analyzer 18. Each of the electrodes 12B have two skin contact points adapted to be attached to selected areas of a human patient 80 as shown in FIG. 2. The electrodes produce a differential analog signal that is representative of the resistance between the two skin contact points of the patient.

The cable assembly 12 is manufactured from light weight materials to prevent or at least minimize the dislodgment of the electrodes 12B and is manufactured in selectable lengths that range from 4 to 40 feet. The cable wiring consist of individual, shielded coax wires that are twisted in pairs for each channel. To eliminate ground loops, each wire shield terminates at an instrumentation amplifier circuit 20A which is the input circuit of the integrated movement analyzer 18 which is described infra. The cable assembly also includes a single, non-coax wire 12C that is used as a signal ground for setting the ground reference from the patient 80 to the integrated movement analyzer 18.

Figure 3:
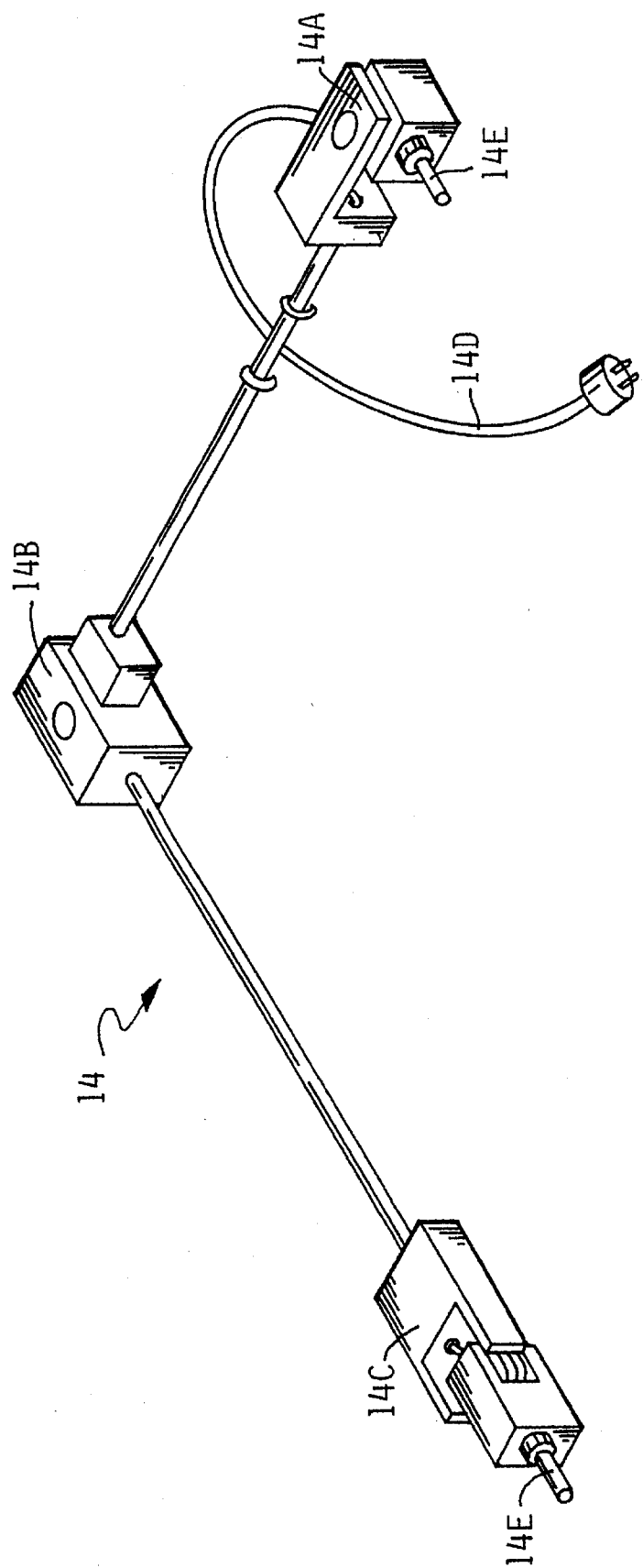
FIG. 3 is a perspective view of the range of motion arm.

The range of motion arm (ROMA) as shown in FIG. 3, includes electrical circuit means and mechanical means for producing range of motion analog signals representative of the angular distance produced from selected areas of the patient 80. The mechanical means is encompassed in a non-load bearing device that includes an upper knuckle 14A, a middle junction 14B and a lower knuckle 14C.

The upper knuckle is designed to rotate in three directions to measure up and down, side to side, and rotary movements of the patient's shoulders for back measurement or the top of the patient's head for cervical movements in the X, Y and Z planes. The middle junction rotates in an angular motion to measure the angular distance in the X-plane, and the lower knuckle rotates in two directions to measure the angular distance in the Y-plane as well as the rotation in the Z-plane.

Figure 4:
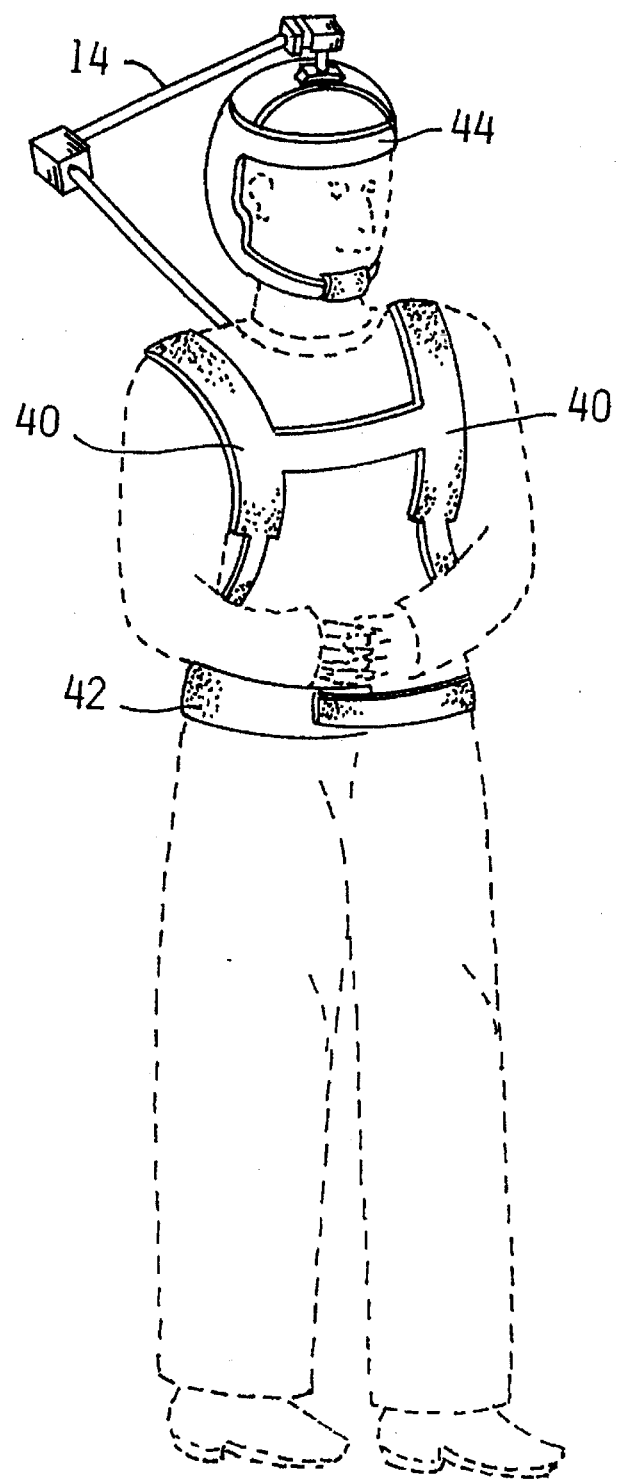
FIG. 4 is a perspective view of a patient that has attached a range of motion arm between a cervical cap and a shoulder harness, and a shoulder harness and a waist belt.
Figure 5:
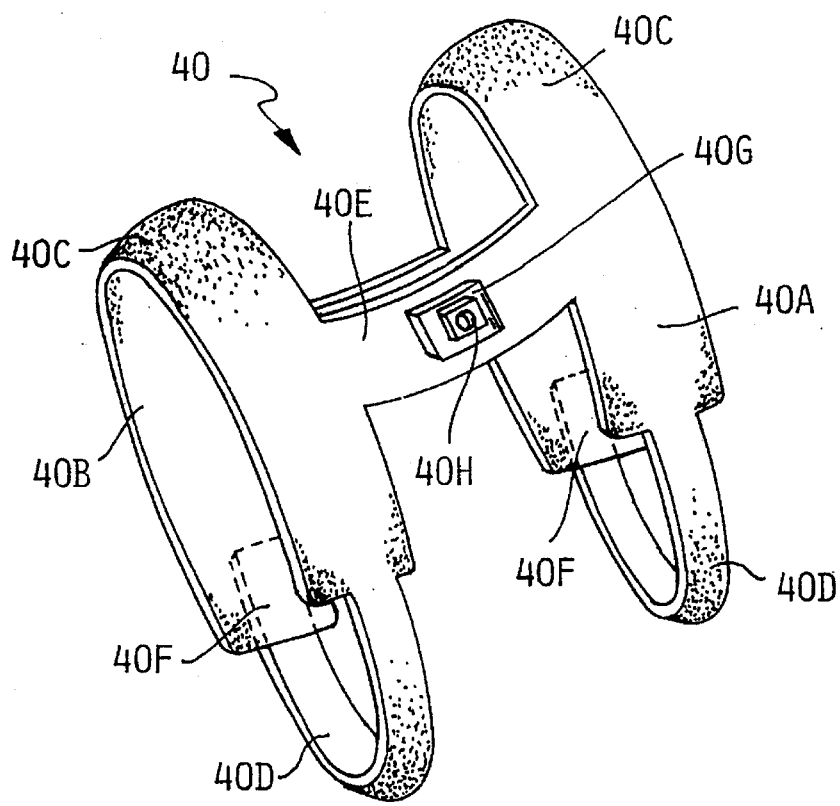
FIG. 5 is a perspective view of the shoulder harness.
Figure 6:
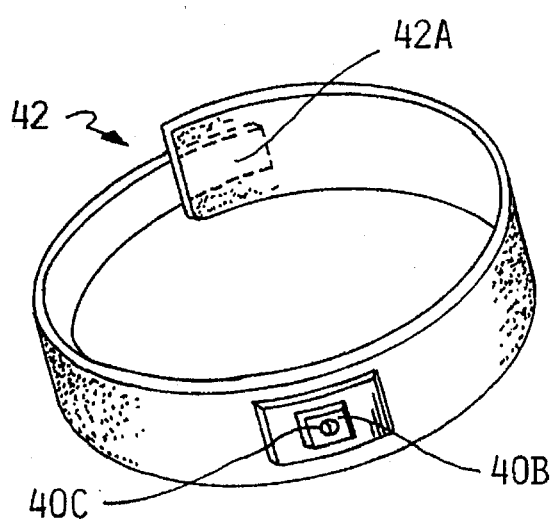
FIG. 6 is a perspective view of the waist belt.
Figure 7:
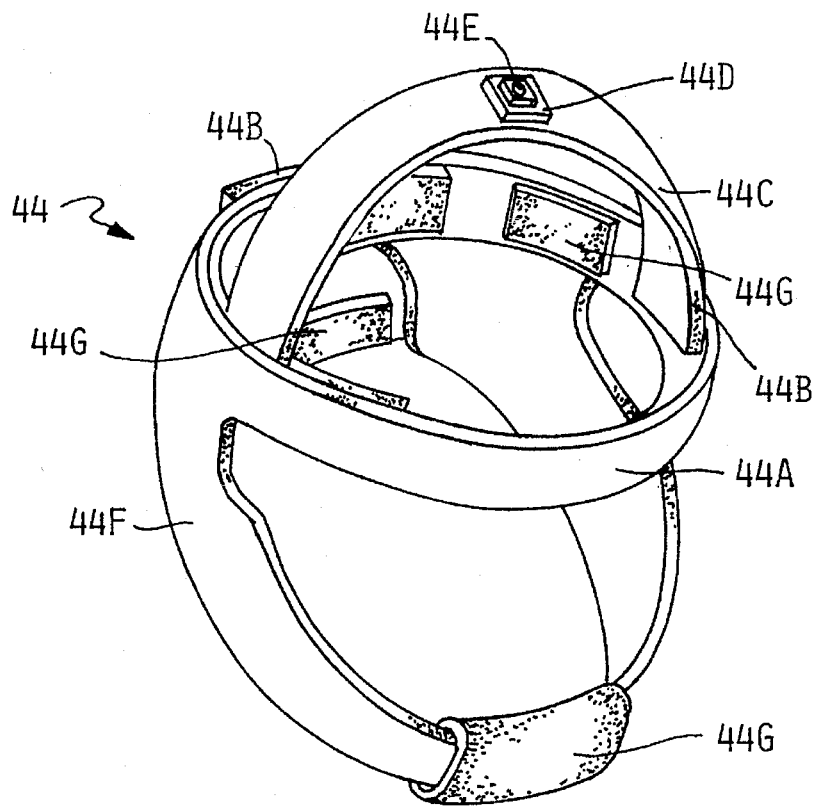
FIG. 7 is a perspective view of a cervical cap.

The ROMA 14, when performing upper back protocol testing, is attached as shown in FIG. 4, from the patient's upper back to the patient's lower back, by means of a shoulder harness 40 as shown in FIG. 5. When performing lower back protocol testing, the ROMA is attached between the shoulder harness 40 and a waist belt 42 as shown in FIGS. 4 and 6. For cervical testing, the ROMA 14 as also shown in FIG. 4, is attached from the top of the patient's head to the patient's upper back, by means of a cervical cap 44 as shown in FIG. 7 and the shoulder harness 40 as shown in FIG. 6.

The ROMA 14 is shown attached in two places in FIG. 4. However, in actual testing, the ROMA 14 is attached to either the cervical cap 44 and the shoulder harness 40, or from the shoulder harness 40 to the waist belt 42.

The shoulder harness 40 as shown in FIG. 5, is typically comprised of a right shoulder support 40A, a left shoulder support 40B, a horizontal back strap 40E and a ROMA attachment structure 40G.

The right and left shoulder supports 40A, 40B each have an upper section 40C and a lower section 40D. The lower sections are looped under the upper arms and are adjustably attached to the upper section by an attachment means 40F that allows the harness 40 to be adjusted to fit the anatomy of the patient 80 undergoing the testing as shown in FIG. 4. The preferred attachment means consists of a complimentary hook and loop fastener 40F as shown in FIG. 5. The horizontal back strap 40E is integrally attached to the inward edges of the back of the right and left shoulder supports 40A, 40B across the upper back of the patient protruding outward from the center of the back strap 40E is the ROMA attachment structure 40G. This structure includes a pin cavity 40H that is sized to accept an attachment pin 14E located on the ROMA 14.

The waist belt 42 as shown in FIG. 6, consists of an attachment means 42A that allows the belt to be adjustably adjusted across the waist of the patient 80 undergoing testing as shown in FIG. 4. The preferred belt attachment means comprises a hook and loop fastener 42A as shown in FIG. 6. Protruding outward from the back of the belt 42 is a ROMA attachment structure 40B. This structure includes a pin cavity 40C that is sized to accept an attachment pin 14E located on the ROMA 14.

The cervical cap 44 as shown in FIG. 7 consists basically of a head band 44A having a means 44B for being adjusted to fit the head of the patient undergoing testing as shown in FIG. 4. Across the head band 44A is attached a head support 44C that includes a means for being adjustably attached to the patient's head. The preferred adjustment means is a complimentary hook and loop fastener 44B. On the center top of the head band 44C is a ROMA attachment structure 44D as shown in FIG. 7, this structure also includes a pin cavity 44E that is sized to accept an attachment pin 14E located on the ROMA 14. As shown in FIG. 7, the cervical cap 44 may also include an adjustable skull mount 44E that has a movable chin support 44G, and resilient head cushions 44H located on the inside of the head band 44A.

The ROMA's 14 electrical circuit means is comprised of a set of potentiometers. The upper knuckle has three potentiometers, the middle junction has one potentiometer, and the lower knuckles has two potentiometers. The potentiometers provide six channels of range of motion analog signals. The range of motion analog signals are in the form of voltage levels ranging from 0 to 5-volts d-c; where 0-volts is representative of 0-degrees of angular displacement and 5-volts d-c is representative of 270-degrees of angular displacement. The analog signals are applied to the IMA 18 through connector 14E of the cable 14D which attaches to IMA connector 18B as described infra.

Figure 8:
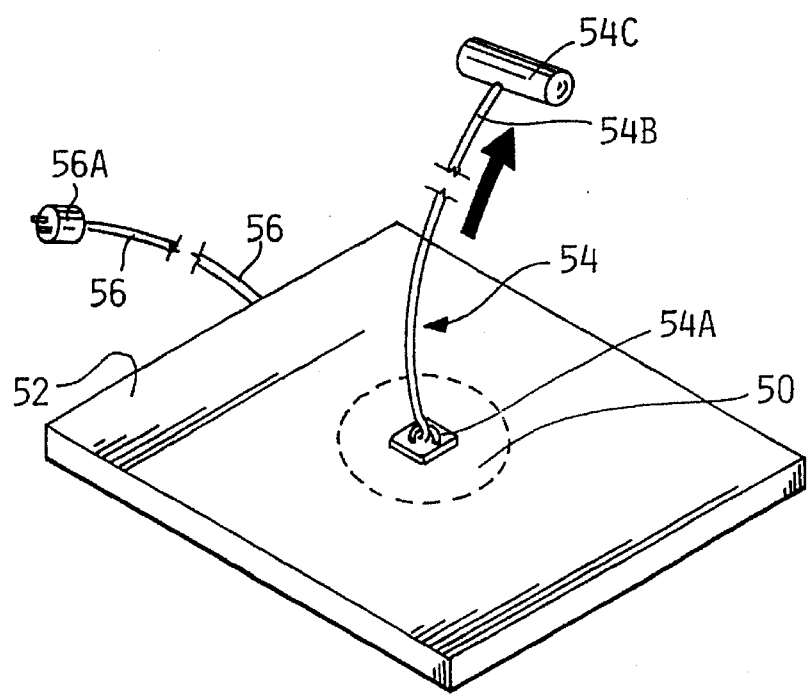
FIG. 8 is a perspective view of a typical functional capacity sensor.

The functional capacity sensor (FCS) as shown in FIGS. 2 and 8, includes electrical circuit means and mechanical means for producing a differential analog d-c signal representative of a pulling force exerted by the patient.

The mechanical means for a preferred embodiment as shown in FIG. 8, is comprised of a strain gauge 50 mounted on a flat metal plate 52 on which the patient stands. Attached to the metal is a pull cable 54 having a first end 54A that is attached to the metal plate 52 and a second end that 54B has attached a two-handed grip 54C. When the grip is pulled by the patient 80, the strain gauge 50 measures the pulling force of the patient which is analogous to the lifting power of the patient.

The lifting force is measured by a range of d-c voltage levels that are representative of the force exerted upon the FCS 16 by the patient 80. The d-c voltage range from 0 to 5-volts, where 0-volts is representative of zero lbs and 5-volts d-c is representative of 400 lbs. The resulting differential analog d-c signals are applied through connector 52 of cable 56 to IMA connector 180 to as described infra.

Figure 9:
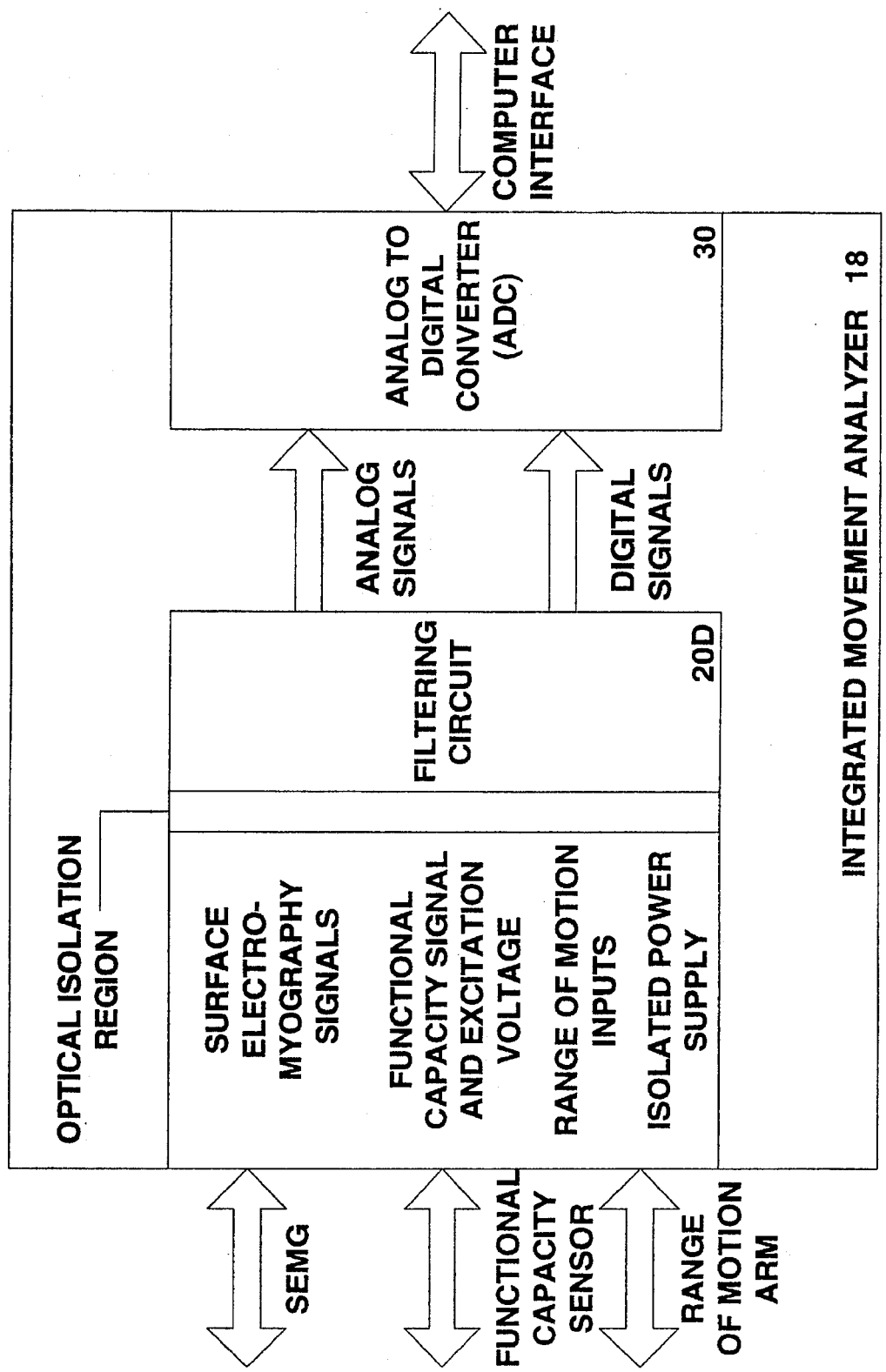
FIG. 9 is an overall block diagram of the integrated movement analyzer.

The integrated movement analyzer (IMA) 18 as shown in FIGS. 2 and 9, is a self contained unit, that is comprised of a surface electromyography section 20 having circuit means for receiving and processing the differential analog signals from the SEMG cable assembly 12; a lead failure detection section 22 having circuit means for receiving and processing the differential analog signals from the SEMG cable assembly 12; a range of motion section 24 having circuit means for receiving and processing the analog signal from the range of motion arm 14; a functional capacity sensing section 26 having circuit means for receiving and processing the analog signals from the functional capacity sensor (FCS) 16 and an isolated power supply section 28 having circuit means for supplying the power required to operate the IMA circuits. The circuit means of the IMA 18 allows the sampling of up to 32 channels of the SEMG analog signals; six channels of the motion arm analog signals and one channel of the functional capacity sensor analog signal, where all the signals are simultaneously measured at sampling speeds of up to 10 KHz at any testing time frame.

Figure 10:
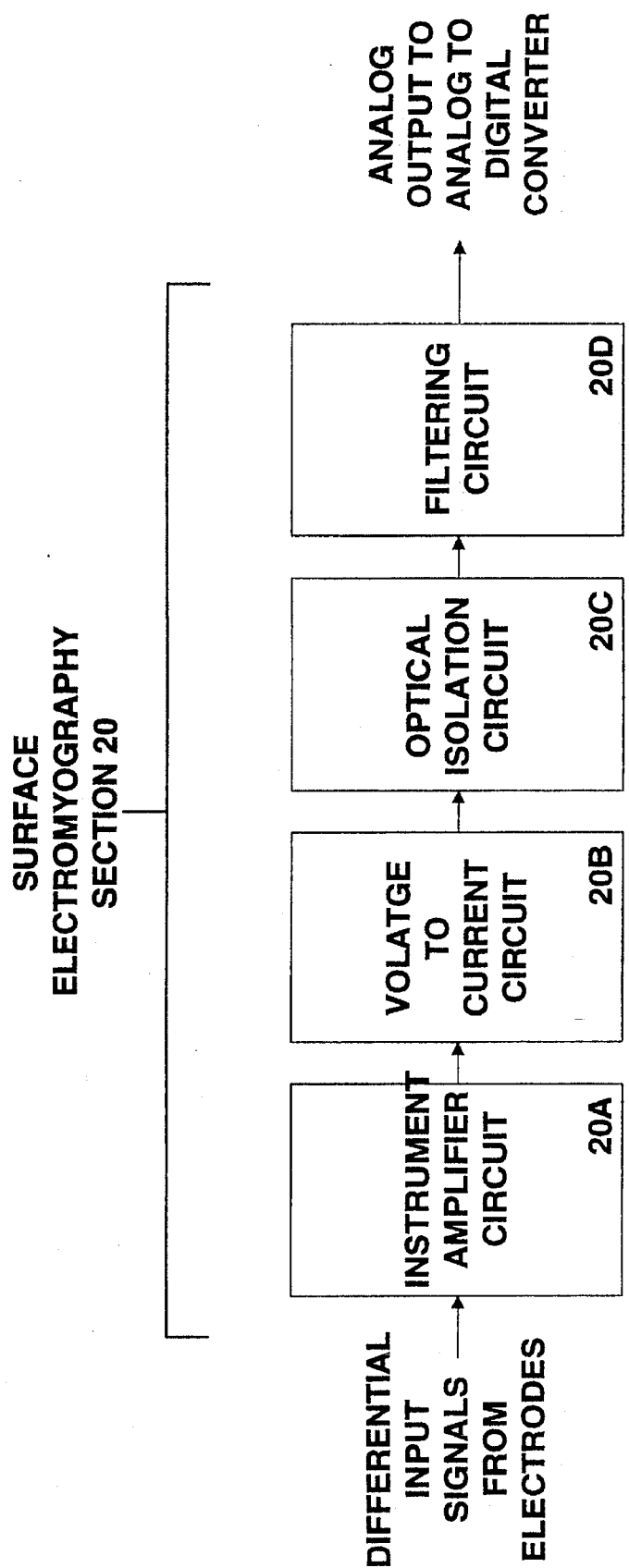
FIG. 10 is a block diagram of the surface electromyography section.

The surface electromyography (SEMG) section 20 circuit means for receiving and processing the differential analog signals from the set of SEMG electrodes 12B, as shown in FIG. 10, comprises: an instrumentation amplifier circuit 20A having means for detecting the resistance between the contact points of each SEMG electrodes 12A, which corresponds to the patient's skin resistance, and converting this resistance to a representative analog voltage. The analog voltage is then applied to a voltage-to-current circuit 20B having circuit means for converting the analog voltage to a linear current drive signal. Following the circuit 20B as shown in FIG. 10 is an optical isolation circuit 20C that isolates the patient 80 from the system 10. The circuit 20C consists of an optically isolated amplifier having circuit means for converting the linear current drive signal to a voltage representative of the differential analog signal from the SEMG electrodes 12A. The final circuit comprising the SEMG section 20 is a filtering circuit 20D that is comprised of:

(1) a 10 Hz high-pass filter that eliminates any d-c component of the output signal from the optical isolation circuit 20C, (2) a notch filter that eliminates 60 Hz are applicable harmonics noise inherently generated in the air, and (3) a low-pass filter that eliminates frequencies above 2.5 KHz. The output signal of the filtering circuit 20D, represents the resistance detected at the SEMG electrode 12B connected to the patient 80.

Figure 11:
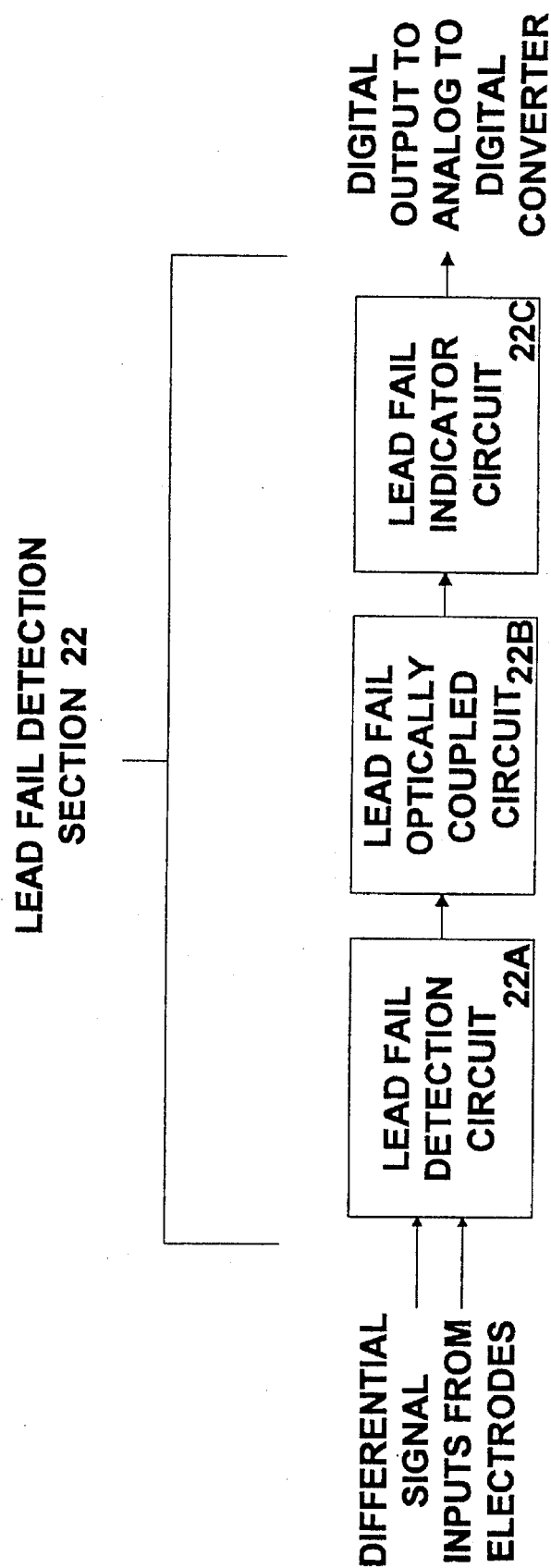
FIG. 11 is a block diagram of the lead failure detection section.

The differential analog signals from the set of SEMG electrode 12B are also applied to a lead failure detection section 22 as shown in FIG. 11. The section 22 comprises a lead-fail detection circuit 22A having means for detecting when the input from the SEMG electrodes 12B cross over a threshold differential voltage level of 5 volts d-c. This voltage level indicates that at least one of two electrode leads 12B has failed. When such a failure occurs, the lead-fail detection circuit 22A produces an output digital signal that is applied to a lead-fail optically coupled circuit 22B. This circuit is comprised of an optical coupler that converts the digital input signal from the lead-fail detection circuit 22A to an isolated optical signal optic then back to a digital signal. The digital signal is applied to a set of lead-fail indicators 22C that consist of light emitting diodes (LED's) that are located on the front panel of the integrated movement analyzer as shown in FIG. 2. The signal that drives the LED's is also sensed by an analog to digital converter and is monitored by the computer software program to allow the particular LED's corresponding to the failed lead, to illuminate so that connection action can be taken to fix the problem.

Figure 12:
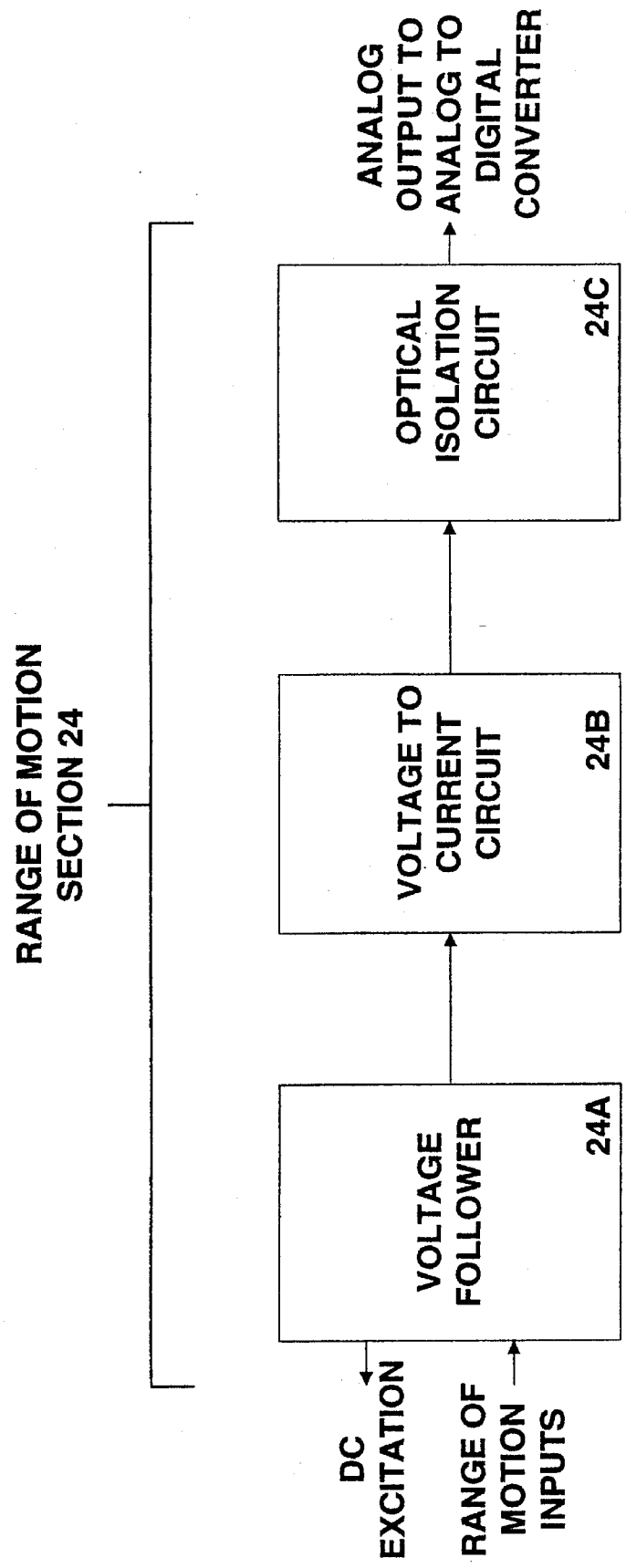
FIG. 12 is a block diagram of the range of motion section.

The range of motion section 24 circuit means as shown in FIG. 12, for receiving and processing the range of motion analog signals produced by the range of motion arm 14 comprises a voltage follower buffering and low-pass filtering circuit 24A having means for:

(1) providing a d-c excitation voltage and an isolated ground that is applied across each of the potentiometers in the range of motion arm (ROMA), (2) retaining the integrity of the potentiometer wiper voltage by eliminating any a-c component above 50 Hz.

From the circuit 24A is produced a processed analog signal that is applied to a voltage-to-current circuit that converts the analog voltages representative of angular distance to a linear current drive signal. In turn, the drive signal is then applied to an isolation circuit consisting of an analog optically isolated amplifier. The amplifier converts the signal to an analog voltage representative of the angular displacement of the ROMA potentiometers.

Figure 13:
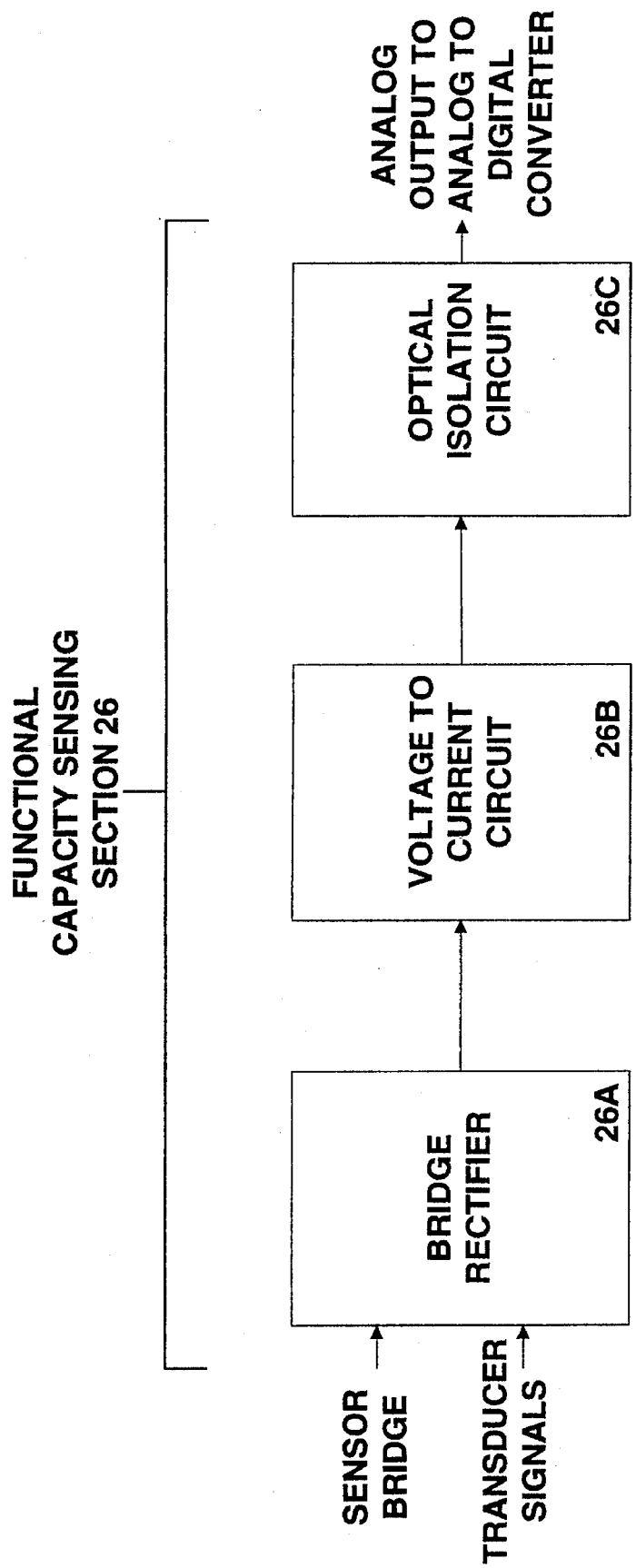
FIG. 13 is a block diagram of the functional capacity sensing section.

The functional capacity sensing section 26 circuit means as shown in FIG. 13 for receiving and processing the differential analog signals supplied by the functional capacity sensor (FCS) 16 is comprised of an instrumentation amplifier circuit and sensor bridge driver voltage 26A having means for:

(1) providing a d-c excitation voltage and an isolated ground for a sensor bridge excitation, (2) receiving a differential signal from the sensor bridge, whereby the difference in resistance is sensed to provide a representative d-c voltage signal.

Following the sensor bridge is a voltage to current circuit 26B which is applied and converts the representative d-c voltage signal to a linear current drive signal. The drive signal is then applied to an optical isolation circuit 26C that isolates the patient 80 from the system 10. The circuit 26C consists of an optically isolated amplifier having circuit means for converting the drive signal signal to a d-c voltage representative of the force exerted upon the FCS. The circuit 26C can be calibrated for variable outputs in a typical calibration, the d-c voltage ranges from 0 to 5-volts, where 0-volts is representative of zero lbs. and 5-volts d-c is representative of 400 lbs.

Figure 14:
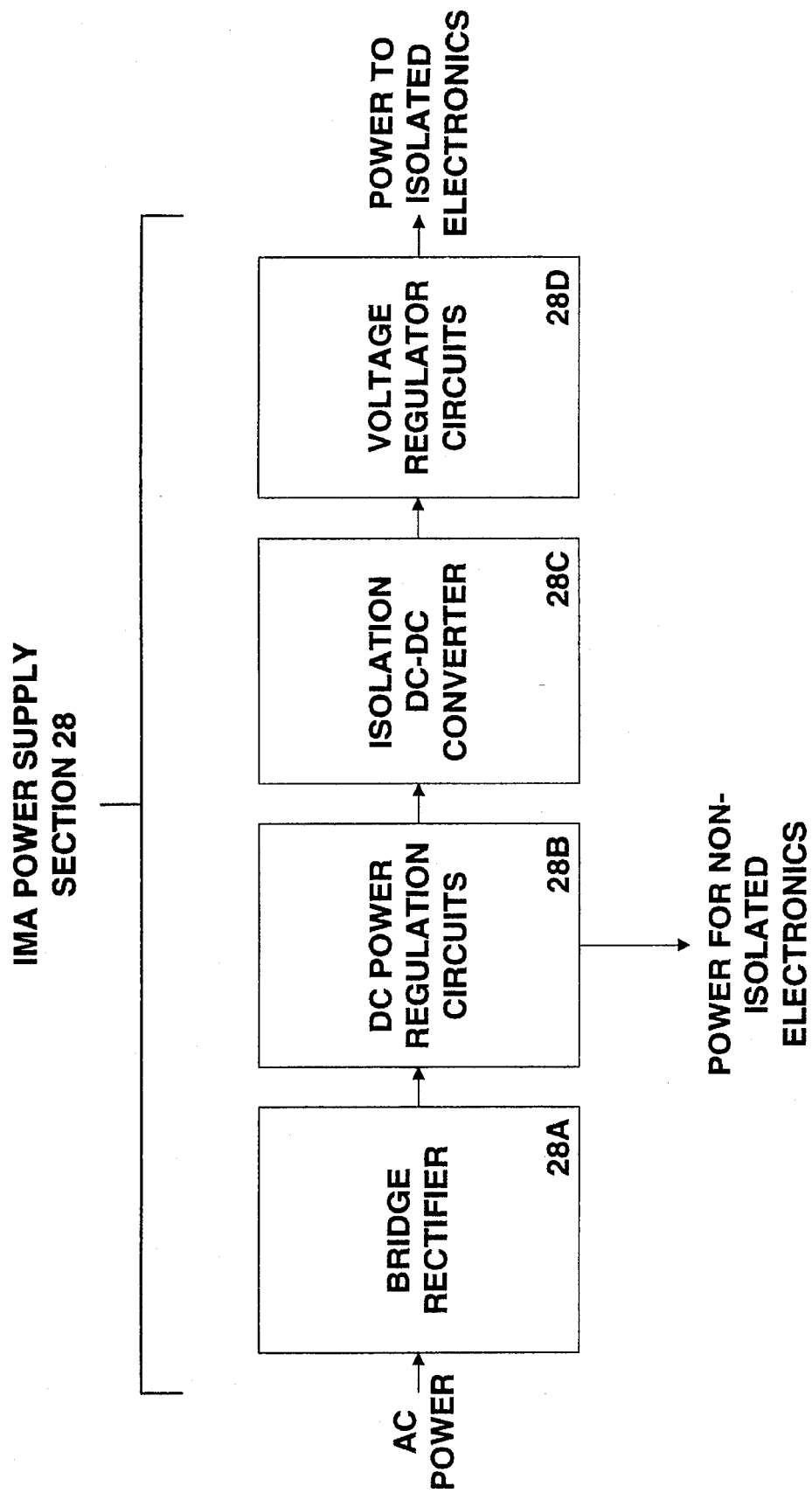
FIG. 14 is a block diagram of the IMA power supply.

The final electronics circuit described is the power supply circuit as shown in FIG. 14. The input to the power supply is derived from the utility 120-volts a-c power which is applied to a bridge rectifier and d-c filter circuit where the a-c utility power is rectified and filtered to produce a d-c voltage output. The d-c voltage is applied a set of d-c power regulation circuits 28B that produce: +5 volts d-c, +12 volts d-c, −12 volts d-c and −5 volts d-c. These voltages are applied:

(1) directly to the system 10 circuits that are not optically isolated, and (2) to a set of isolated d-c to d-c converting circuit 28C that convert the non-isolated d-c voltages to isolated d-c voltages, and (3) to an isolated ±5 volts d-c and ±12 volts d-c voltage regulator circuit 28D which further regulate and produce the d-c regulated voltages required for the optically isolated circuits.

From the respective SEMG, ROMA and FCS sections as shown in FIG. 9, the respective output signals are applied to an analog-to-digital converter (ADC) for further processing. The ADC in the preferred embodiment is a 16 bit, 16 channel device that also includes 8 lines of digital I/O. However, multiple assemblies can be connected to provide up to 32 channels.

The processed signals from the ADC 30 are terminated at an output connector such as an IEEE 488 interface. From the interface connector, the signals are routed through a cable assembly 32 and applied to a computer 32 shown in FIG. 2. The computer 34 operates with a software program 36 to produce the comparative analytical data representative of the patient's problem being analyzed. The software program which is protected under registered and pending copyright registrations:

a) interfaces with a parallel interface connector, b) selects the voltage level that each channel will respond to, c) initializes the sampling frequency rate of the ADC, d) selects the appropriate testing protocol, e) samples each cable led during the test to detect if a lead failure has occurred, f) prompts the system 10 user as to the location of a lead failure, g) starts the integrated movement analyzer when the testing should begin, h) prompts the technician as to the muscle groups that the individual leads should be connected to for a given protocol, i) prompts the technician as to the activities that the patient should be performing during the test cycle, j) saves the data on hard drive at the completion of a test, k) converts the patient's data from binary data to computer graphics, l) time and date stamps each file as data is taken, m) generates computer plots from 1 to 40 channels of data, n) plots range of motion data and correlates this data to angular displacement, o) plots functional capacity data and correlates this data to maximum force applied to the functional capacity sensor by the patient, p) sets the testing time for the test being performed, and q) produces plots which include patient information, location of test, the test performed and the muscle groups.

While the invention has been described in complete detail and pictorially shown in the accompanying drawings it is not to be limited to such details, since many changes and modifications may be made to the invention without departing from the spirit and the scope thereof. Hence, it is described to cover any and all modifications and forms which may come within the language and scope of the claims.

I claim:

1. An integrated movement analyzing system comprising:

a) a surface electromyography (SEMG) cable assembly having on one end a cable connector and on the other end a set of electrodes, with each electrode having two skin contact points adapted to be attached to selected areas of a human patient, where each said SEMG electrode produces a differential analog signal representative of the resistance between the two skin contact points of the patient, b) a range of motion arm (ROMA) having electrical circuit means and mechanical means for producing range of motion analog signals representative of the angular distance produced from selected areas of the patient, c) a functional capacity sensor (FCS) having circuit means for producing a differential analog d-c signal representative of a pulling force exerted by the patient, d) an integrated movement analyzer (IMA) comprising:

(1) a surface electromyography section having circuit means for receiving and processing the analog signals from the electrodes attached to said SEMG cable assembly, (2) a range of motion section having circuit means for receiving and processing the analog signals from said ROMA, (3) a functional capacity section having circuit means for receiving and processing the analog signals from said FCS, and (4) an analog to digital converter (ADC) that receives and further processes the SEMG electrode, ROMA and FCS analog signals from said respective section, e) an isolated power supply having circuit means for supplying the power requirements for operating the circuits of said integrated movement analyzing system, and f) a computer and software program that receive the processed signals from said ADC for further processing and for the production of data representative of the patient's problems being analyzed.

2. The system as specified in claim 1 wherein said integrated movement analyzer has circuit means for sampling up to 32 channels of the differential surface electromyography analog signals, six channels of the range of motion arm analog signals and one channel of the functional capacity sensor analog signal, where all the signals are simultaneously measured at sampling speeds of up to 10 KHz for testing time frames.

3. The system as specified in claim 2 wherein said integrated movement analyzer circuit means for receiving and processing the differential analog signals from said set of surface electromyography (SEMG) electrodes comprises:

a) an instrumentation amplifier circuit having means for detecting the resistance between the contact point of each SEMG electrodes which corresponds to the patient's skin resistance and muscle activity and converting this resistance to a representative analog voltage, b) a voltage-to-current circuit that is applied the analog voltage from said instrumentation amplifier circuit and having circuit means for converting the analog voltage to a linear current drive signal, c) an optical isolation circuit that isolates the patient from said system and that is comprised of an analog optically isolated amplifier having circuit means for converting the linear current drive signal to a voltage representative of the differential analog signal from said SEMG electrodes, and d) a filtering circuit comprising:
  (1) a 10 Hz high-pass filter that eliminates any d-c component of the output signal from said 2.5 KV optical isolation circuit,
  (2) a notch filter that eliminates 60 Hz and applicable harmonics noise inherently generated in the air, and
  (3) a low-pass filter that eliminates frequencies above 2.5 KHz, where the output signal of said filtering circuit represents the resistance detected at the SEMG electrode connected to the patient.

4. The system as specified in claim 2 wherein said integrated movement analyzer further consists of a lead failure detection section that alerts a system operator when there is a lead failure, where said lead failure detection section comprises:

a) a lead-fail detection circuit having means for detecting when the input from said SEMG electrodes cross over a threshold differential voltage level of 5 volts d-c indicating that at least one of the two said electrode leads has failed, where upon such a failure, said lead-fail detection circuit produces an output digital signal, b) a lead-fail optically coupled signal circuit that is comprised of an optical coupler that converts the digital input signal from said lead-fail detection circuit to an isolated optical signal optic then back to a digital signal, and c) a set of lead-fail indicators comprising light emitting diodes (LED's) that are located on a front panel of said integrated movement analyzer, where the signal that drives said LED's is also sensed by said analog to digital converter and is monitored by said computer software program to allow the particular LED, corresponding to the failed lead, to illuminate.

5. The system as specified in claim 1 wherein said range of motion arm (ROMA) mechanical means comprises a non-load bearing device that includes an upper knuckle, a middle junction and a lower knuckle, where said ROMA is attached, by an attachment means, from the patient's shoulders to the patient's lower back for back protocol testing or from the patient's head to the patient's shoulder for cervical testing, wherein said ROMA's:

a) upper knuckle rotates in three directions to measure up and down, side to side, and rotary movements of the patient's shoulders for back measurements or the top of the patient's head for cervical movements in the X, Y and Z planes, b) middle junction rotates in an angular motion to measure the angular distance in the X-plane, and c) lower knuckle rotates in two directions to measure the angular distance in the Y-plane as well as the rotation in the Z-plane.

6. The system as specified in claim 5 wherein said means for attaching said range of motion arm from the patient's upper back to the patient's lower back comprises a shoulder harness and a waist belt respectively.

7. The system as specified in claim 5 wherein said means for attaching said range of motion arm from the patient's upper back to the patient's head comprises a shoulder harness and a cervical cap respectively.

8. The system as specified in claim 6 wherein said shoulder harness comprises:

a) a right shoulder support having an upper section and a lower section, where the lower section is adjustably attached to the upper section by an attachment means that allows the right shoulder support to be adjusted to fit the anatomy of the patient undergoing testing, b) a left shoulder support having an upper section and a lower section, where the lower section is adjustably attached to the upper section by an attachment means that allows the left shoulder support to be adjusted to fit the anatomy of the patent being tested, and c) a horizontal back strap that is integrally attached to the inward back edges of the right and left shoulder supports across the upper back of the patient, where protruding outward from the center of the back strap is a ROMA attachment structure that allows said ROMA to be removably attached.

9. The system as specified in claim 6 wherein said waist belt comprises:

a) a means for adjustably attaching said waist belt across the waist of the patient undergoing testing and, b) a ROMA attachment structure that protrudes outward from the back of said waist belt and that allows said ROMA to be removably attached.

10. The system as specified in claim 7 wherein said cervical cap comprises:

a) a head band having means for being adjusted to fit the head of the patient undergoing testing, b) a head support that is attached across the head band, and c) a ROMA attachment structure that protrudes outward from the top of the head support and allows said ROMA to be removably attached.

11. The system as specified in claim 1, wherein said range of motion arm (ROMA) circuit means comprises a set of potentiometers where said ROMA's upper knuckle has three potentiometers, the middle junction has one potentiometer, and the lower knuckles has two potentiometers where the potentiometers provide six channels of range of motion analog signals.

12. The system as specified in claim 11 wherein the range of motion analog signals from said ROMA are in the form of voltage levels ranging from 0 to 5-volts d-c, where 0-volts is representative of 0-degrees of angular displacement and 5-volts d-c is representative of 270-degrees of angular displacement.

13. The system as specified in claim 11 wherein said integrated movement analyzer circuit means for receiving and processing the range of motion analog signals from said range of motion arm comprises:
   a) a voltage follower buffering and low-pass filtering circuit having means for:
      (1) providing a d-c excitation voltage and an isolated ground that is applied across each of the potentiometers in said ROMA,
      (2) retaining the integrity of the potentiometer wiper voltage by eliminating any a-c component above 50 Hz,
   b) a voltage-to-current circuit that receives the processed analog signal from said voltage follower buffering and low-pass filtering circuit and converts the analog voltages representative of angular distance to a linear current drive signal, and
   c) an isolation circuit consisting of an analog optically isolated amplifier which receives the linear current drive signal from said voltage-to-current circuit and converts the signal to a voltage representative of the angular displacement of the ROMA potentiometers.

14. The system as specified in claim 1 wherein said integrated movement analyzer circuit means for receiving and processing the differential analog d-c signals from said functional capacity sensor (FCS) comprises:
   a) an instrumentation amplifier circuit and sensor bridge driver voltage having means for:
      (1) providing a d-c excitation voltage and an isolated ground for sensor bridge excitation,
      (2) receiving a differential signal from said sensor bridge, whereby the difference in resistance is sensed to provide a representative d-c voltage signal,
   b) a voltage to current circuit which is applied and converts the representative d-c voltage signal to a linear current drive signal, and
   c) an optical isolation circuit consisting of an optically isolated amplifier which receives the linear current drive signal from said voltage to current circuit and converts the signal to a d-c voltage representative of the force exerted upon said FCS.

15. The system as specified in claim 14 wherein the range of voltage levels for the d-c voltage representative of the force exerted upon said FCS range from 0 to 5-volts, where 0-volts is representative of zero lbs. and 5-volts d-c is representative of the specific calibration of the sensor bridge.

16. The system as specified in claim 15 wherein said functional capacity sensor mechanical means comprises:
   a) a strain gauge mounted on a flat piece of metal on which the patient stands, and
   b) an adjustable cable having an end attached to the flat piece of metal and the other end having a two handed grip, where when the grip is pulled by the patient, the strain gauge measures the pulling force of the patient which is analogous to the lifting power of the patient.

17. The system as specified in claim 1 wherein said power supply circuit comprises:
   a) a bridge rectifier and d-c circuit filter that is applied a-c utility power which is then rectified and filtered to produce a d-c voltage output,
   b) a set of d-c power regulation circuits that are applied the d-c voltage from said bridge rectifier and d-c filter and that produce: +5 volts d-c, +12 volts d-c, −12 volts d-c and −5 volts d-c which are applied:
      (1) directly to said system circuits that are not optically isolated, and
      (2) to a set of isolation d-c to d-c converting circuits that convert the non-isolated d-c voltages to isolated d-c voltages, and
      (3) to an isolated ±5 volts d-c and ±12 volts d-c voltage regulators which further regulate and produce the d-c regulated voltages required for the optically isolated circuits.

18. The system as specified in claim 1 wherein said surface electromyography cable assembly that houses the SEMG electrodes varies in length from 4 to 40 feet in configurations consisting of individual shielded coax wires twisted in pairs for each channel, where the shields for each wire terminate at the input circuit of said integrated movement analyzer to eliminate ground loops, and where said cable further includes a single, non-coax wire that is used as signal ground for setting the ground reference from the patient to the integrated movement analyzer, where said cable terminates at the integrated movement analyzer with a twist lock connector and the patient end of the cable has terminations for electrodes.

19. The system as specified in claim 1 wherein said data produced by said combination computer and software program produces comparative analytical data which is in the form of graphic plots.

20. The system as specified in claim 19 wherein said computer software:
   a) interfaces with a parallel interface connector,
   b) selects the voltage level that each channel will respond to,
   c) initializes the sampling frequency rate of the ADC,
   d) selects the appropriate testing protocol,
   e) samples each cable lead during the test to detect if a lead failure has occurred,
   f) prompts the system user as to the location of a lead failure,
   g) starts the integrated movement analyzer when the testing should begin,
   h) prompts the technician as to the muscle groups that the individual leads should be connected to for a given protocol,
   i) prompts the technician as to the activities that the patient should be performing during the test cycle,
   j) saves the data on hard drive at the completion of a test,
   k) converts the patient's data from binary data to computer graphics,
   l) time and date stamps each file as data is taken,
   m) generate computer plots from 1 to 40 channels of data,
   n) plots range of motion data and correlates this data to angular displacement,
   o) plots functional capacity data and correlates this data to maximum force applied to the functional capacity sensor by the patient,
   p) sets the testing time for the test being performed, and
   q) produces plots which include patient information, location of test, the test performed and the muscle groups.

* * * * *